US005759941A

United States Patent [19]

Saleh

[11] Patent Number: 5,759,941
[45] Date of Patent: Jun. 2, 1998

[54] PROCESS FOR THE PREPARATION OF DIALKYLTIN DIALKOXIDE FROM ALKYL CARBAMATE AND ALCOHOL

[75] Inventor: Ramzi Yanni Saleh, Flemington, N.J.

[73] Assignee: Exxon Chemical Patents Inc, Houston, Tex.

[21] Appl. No.: 387,413

[22] Filed: Feb. 10, 1995

[51] Int. Cl.$^6$ ........................................................ B01J 31/00
[52] U.S. Cl. ........................... 502/152; 502/161; 502/162; 502/170; 502/171; 556/88; 556/89
[58] Field of Search ............................ 502/152, 161, 502/162, 170, 171; 556/88, 89

[56] References Cited

U.S. PATENT DOCUMENTS

| | | |
|---|---|---|
| 2,583,084 | 1/1952 | Burt . |
| 2,700,675 | 1/1955 | Mack et al. . |
| 2,727,917 | 12/1955 | Mack et al. . |
| 3,492,327 | 1/1970 | Davies . |
| 5,545,600 | 8/1996 | Knudsen et al. ................ 502/152 |

FOREIGN PATENT DOCUMENTS

| | | | |
|---|---|---|---|
| 0 569 845 | 5/1993 | European Pat. Off. ......... | C07F 7/22 |
| 664133 | 1/1952 | United Kingdom . | |

OTHER PUBLICATIONS

Davies et al., "Organotin Chemistry. Part XI. The Preparation of Organotin Alkoxides", *Journal of Chemical Society*, 1971, pp. 3972–3976, no month available.

M.G. Voronkov and Yu P. Romadan, New Method for the Synthesis of Dialkyoxydialkyltins, *Zhurnal Obshchei Khimii*, vol. 39, No. 12, pp. 2785–2786, Dec. 1969.

*Primary Examiner*—Elizabeth D. Wood
*Attorney, Agent, or Firm*—John F. Hunt

[57] ABSTRACT

A process for making a catalyst product which comprises reacting dialkyltin oxide with an alcohol and the corresponding alkyl carbamate at a temperature in the range between about 160 to 190° C. and at an autogenous pressure, wherein the catalyst product comprises dialkyltin dialkoxide in the range between about 50 to 100 mole % based on the tin species of the catalyst product.

21 Claims, No Drawings

PROCESS FOR THE PREPARATION OF DIALKYLTIN DIALKOXIDE FROM ALKYL CARBAMATE AND ALCOHOL

The present invention relates generally to the synthesis of dialkyltin dialkoxide (e.g., dibutyltin dimethoxide) from dialkyltin oxide. The dialkyltin oxide is treated with an alcohol and the corresponding alkyl carbamate at elevated temperature and autogenous pressure to produce dialkyltin dialkoxide in quantitative yields.

BACKGROUND OF THE INVENTION

One method for the preparation of dibutyltin dimethoxide involves the reaction of dibutyltin dichloride with sodium methoxide (Equation 1). This method of synthesis is described in U.S. Pat. No. 2,700,675 Mack et al.) and is shown below:

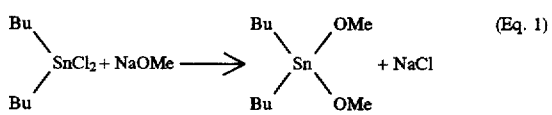

The crude dibutyltin dimethoxide is then purified by vacuum distillation. The relatively high cost of dibutyltin dimethoxide using the above process has prompted an investigation of alternative synthetic routes using relatively inexpensive starting materials.

Dibutyltin dialkoxides of higher alcohols have been synthesized by transesterification of dibutyltin dimethoxide with alcohols such as 1-dodecanol. This process is described in U.S. Pat. No. 2,727,917 (Mack et al.) and is shown below in Equation 2:

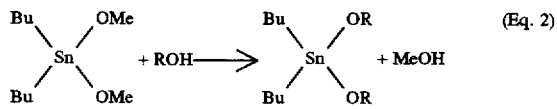

Also, dialkoxides of primary alcohols have been synthesized via a two step reaction. The first step involves condensation of dibutyltin oxide with a primary alcohol in refluxing benzene or toluene at 80°–110° C., to produce 1,3-bis(alkoxy)tetrabutyl distannoxane. Water which is formed as a product in the condensation reaction is removed by azeotropic distillation. In the second step the distannoxane undergoes disproportionation at 180°–220° C. under reduced pressure to produce dibutyltin oxide and dibutyltin dialkoxide as shown below in Equation 3:

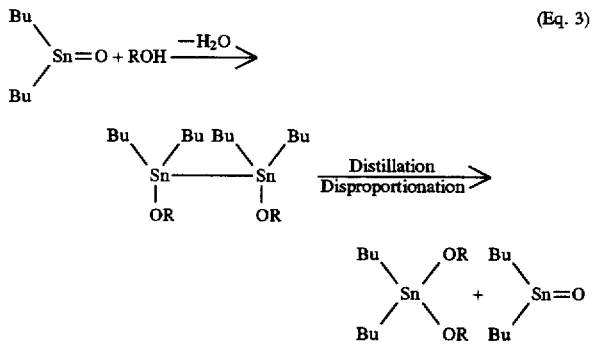

It should be noted, however, that secondary alcohols do not react with dibutyltin oxide in this way.

The method illustrated by the reactions shown in Equation 3 does not work for methanol which does not form an azeotrope with water. Treatment of dibutyltin oxide with methanol and toluene at temperatures ranging from 115°–180° C. and pressures varying from ambient to 2.756 Mpa (400 psi) results in the formation of 1,3 bis(methoxy) tetrabutyl distannoxane, but does not produce the desired dibutyltin dimethoxide in any significant yield.

An alternative route involving the reaction of dibutyltin oxide with dimethyl carbonate (in the presence of traces of methanol) to produce 1,3bis(methoxy)tetrabutyl distannoxane exclusively is described in an article by Davies et al., entitled "Organic Chemistry, Part XI—The Preparation of Organotin Alkoxides", Journal of Chemical Society, (C) (1971), pp. 3972–6. The reaction according to the Davies article is conducted in the presence of toluene at 80°–110° C. and 1 atmosphere pressure.

The present inventor has surprisingly discovered that the addition of methyl carbamate as a reactant to a mixture of dibutyltin oxide and alcohol, at elevated temperatures and autogenous pressure results in quantitative yields of dibutyltin dimethoxide along with the evolution volatile fractions and unused alcohol from the reaction vessel. The present process can be run continuously if volatile fractions formed during the reaction, and excess alcohol and portions of the product are periodically removed from the reaction vessel and replaced with fresh alcohol and alkyl carbamate (e.g., methyl carbamate).

Hence, the present inventor has discovered a unique low cost synthetic route to dibutyltin dimethoxide. Dibutyltin dimethoxide is a highly effective catalyst in numerous applications such as transesterification, esterification, ester interchange, transamination, and the synthesis of organic carbonates by the reaction of alcohols with alkyl carbamates and/or urea. The catalyst prepared by this technique may be used without purification thereby achieving an additional cost savings. This compound, as mentioned previously, is a starting material for the synthesis of dibutyltin alkoxides based on higher molecular weight alcohols as shown in Equation 2 above.

The present invention can also be used as a means of recycling and reactivating partially spent tin catalysts from the aforementioned applications by reconverting the inactive tin compounds to the dialkyltin dialkoxide by treatment with water followed by treatment with alcohol and alkyl carbamate as described herein.

The present invention also provides many additional advantages which shall become apparent as described below.

SUMMARY OF THE INVENTION

A process for making a catalyst product which comprises reacting dialkyltin oxide with either a primary or secondary alcohol (e.g., methanol) and alkyl carbamate at a temperature in the range between about 160°–190° C. and at an autogenous pressure (i.e., depends on the vapor pressure of the alcohol and alkyl carbamate), typically in the range between about 1.58 to 3.44 MPa (230 to 500 psig), wherein the catalyst product comprises dialkyltin dialkoxide in the range between about 50 to 100 mole % (based on tin species within the catalyst product), more preferably about 70 to 100 mole %, and most preferably between about 90 to 98 mole %. Preferably, the dialkyltin oxide is dibutyltin oxide and the alkyl carbamate is methyl carbamate, thereby producing dibutyltin dimethoxide. The reaction time required for quantitative conversion to dimethoxide is typically between about 1 to 6 hours.

The primary and secondary alcohols are preferably selected from the group consisting of $C_1$ to $C_{12}$ primary and secondary alcohols, respectively.

The present invention also encompasses a process for recycling or reactivating partially spent tin catalysts (e.g., dialkyltin dicarboxylate catalysts or dialkyltin dialkoxide catalysts) generated from applications such as transesterification, esterification, ester interchange, transamination, and the synthesis of organic carbonates by reconverting the inactive or spent tin compounds to the dialkyltin dialkoxide by treatment with water, followed by treatment with alcohol and alkyl carbamate as described herein. For example, a dialkyl carbonate reaction product synthesized from organic carbamates typically comprises alkyl carbamate, alkylated by-products, dialkyl carbonates, dialkyltin dialkoxide catalyst and carbonate-forming alcohol. The tin catalyst used during the synthesis of dialkyl carbonates is reactivated or regenerated by the following steps: separating the dialkyltin dialkoxide catalyst from the dialkyl carbonate reaction product thereby forming a dialkyltin dialkoxide catalyst-enriched stream and a dialkyltin dialkoxide catalyst-poor stream; reacting the dialkyltin dialkoxide catalyst-enriched stream with water to form a dialkyltin oxide stream; drying the dialkyltin oxide stream; reacting the dialkyltin oxide stream with a reactivation alcohol and alkyl carbamate thereby forming a reactivated dialkyltin dialkoxide catalyst stream; and recycling the reactivated dialkyltin dialkoxide catalyst stream to the reaction vessel.

Alternatively, dialkyltin dialkoxide catalysts may be synthesized adding urea product or the like and excess alcohol at a temperature in the range between about 155° C. to 190° C., preferably 155° C. to 170° C., and an autogenous pressure, wherein the alcohol converts the urea in-situ to an alkyl carbamate which then reacts with the excess alcohol to form the dialkyltin dialkoxide catalyst. Autogenous pressure is used such that volatile fractions formed during the reaction and alcohol are removed from the reaction vessel and replaced with fresh alcohol.

The present invention also encompasses a process for recycling or reactivating partially spent tin catalysts (e.g., dialkyltin dicarboxylate catalysts or dialkyltin dialkoxide catalysts) generated from applications such as transesterification, esterification, ester interchange, transamination, and the synthesis of organic carbonates by reconverting the inactive or spent tin compounds to the dialkyltin dialkoxide by treatment with water, followed by treatment with alcohol and dialkyl carbonate as described herein. For example, a dialkyl carbonate reaction product synthesized from organic carbonates typically comprises alkyl carbamate, alkylated by-products, dialkyl carbonate, dialkyltin dialkoxide catalyst and carbonate-forming alcohol. The tin catalyst used during the synthesis of organic carbonates is reactivated or regenerated by the following steps: separating the dialkyltin dialkoxide catalyst from the dialkyl carbonate reaction product thereby forming a dialkyltin dialkoxide catalyst-enriched stream and a dialkyltin dialkoxide catalyst-poor stream; reacting the dialkyltin dialkoxide catalyst-enriched stream with water to form a dialkyltin oxide stream with a reactivation alcohol and alkyl carbamate thereby forming a reactivated dialkyltin dialkoxide catalyst stream; and recycling the reactivated dialkyltin dialkoxide catalyst stream to the reaction vessel.

DESCRIPTION OF THE PREFERRED EMBODIMENTS

Dibutyltin oxide is reacted with methanol and methyl carbamate, at a temperature in the range between about 160 to 190° C. and at an autogenous pressure resulting in a quantitative formation of dibutyltin dimethoxide (i.e., dibutyltin dimethoxide is present in the final product in an amount between about 50 to 100 mole % (based on tin species in the catalyst product), more preferably about 70 to 100 mole %, and most preferably 90–98 mole %).

The dibutyltin oxide is present in an amount of about 1 to 25 mole %, based on the total reaction mixture. The alcohol is present in an amount of about 10 to 90 mole %, based on the total reaction mixture. The methyl carbamate is present in an amount of about 20 to 90 mole %, based on the total reaction mixture. The molar ratio of the alcohol to the methyl carbamate is in the range between about 10:1 to 1:4.

Operating with sufficient pressure is important so far as it enables one to attain high enough temperatures for the reaction to proceed. As such, temperature is a critical variable, while pressure is only helpful in reaching the desired temperatures and satisfactory rates of conversion.

Optionally, the process according to the present invention can provide for the in-situ formation of alkyl carbamate from urea or the like and in the presence of excess alcohol at a temperature in the range between about 155° C. to 190° C., more preferably between about 155° C. to 170° C., and at an autogenous pressure. The conversion of urea to alkyl carbamate is described by the equation immediately below:

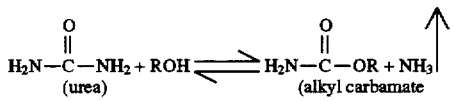

where R is any aliphatic, cycloaliphatic, araliphatic, arylcycloaliphatic, heterocyclic aliphatic, or non-aromatic heterocyclic monohydric group comprising from about 1 to 16 carbon atoms. This conversion involves the reaction of urea or the like with an alcohol (e.g., methanol) at temperatures and pressures such that the alcohol which contains the NH$_3$ (a reaction product) is allowed to distilled from the reactor and which is replaced with fresh alcohol to maintain a constant level in the reactor. Urea can also be added to the reactor for a continuous operation. In this case alkyl carbamate and alcohol/NH$_3$ are continuously distilled from the reactor and replaced with urea and fresh alcohol. Under these conditions, the equilibrium in the equation above is shifted to the right.

Thereafter, the alkyl carbamate formed from the urea reacts with the remaining alcohol at a temperature in the range between about 160 to 190° C. and at an autogenous pressure resulting in a quantitative formation of dibutyltin dimethoxide (i.e., dibutyltin dimethoxide is present in the final product in an amount between about 50 to 100 mole % (based on tin species in the catalyst product), more preferably about 70 to 100 mole %, and most preferably 90–98 mole %).

The urea product is preferably selected from the group consisting of urea, N-alkyl substituted urea, N,N-dialkyl ureas, N,N'-dialkyl ureas, trialkyl ureas and tetraalkyl ureas.

The dialkyltin oxide is present in an amount of about 1 to 25 mole %, based on the total reaction mixture. The alcohol is present in an amount of about 50 to 90 mole %, based on the total reaction mixture. The urea product is present in an amount of about 50 to 90 mole %, based on the total reaction mixture. The molar ratio of alcohol to urea product is in the range between about 10:1 to 1:1.

The alcohols used according to the present invention can be any primary or secondary alcohols. The primary and secondary alcohols may be selected from the group consisting of $C_1$ to $C_{12}$ alcohols, more preferably between about $C_1$ to $C_8$ alcohols, and most preferably between about $C_1$ to $C_5$ alcohols. Alcohols which are most suited for use in converting dialkyltin oxide to dialkyltin dialkoxide in the presence of alkyl carbamate are methanol, ethanol, n-propanol, isopropanol, n-butanol, isobutanol, sec-butanol, n-pentanol, 2-pentanol, 3-pentanol, isopentanol, n-octanol, cyclohexanol, n-dodecanol, isododecanol, etc.

The catalyst according to the present invention can be used to synthesize dimethyl carbonate (DMC) which is an important industrial chemical. DMC is preferably prepared via a two step process. The first step involves the synthesis of alkyl carbamate from urea or the like and an alcohol, i.e., ROH, where R is any aliphatic, cycloaliphatic, arylaliphatic, arylcycloaliphatic, heterocyclic aliphatic, or non-aromatic heterocyclic monohydric group comprising from about 1 to 16 carbon atoms. This step involves the reaction of urea or the like with an alcohol (e.g., methanol) at temperatures and pressures such that the alcohol which contains the $NH_3$ (a reaction product) is allowed to distill from the reactor and which is replaced with fresh alcohol or recycled to maintain a constant level in the reactor. Urea can also be added to the reactor for a continuous operation. In this case alkyl carbamate and alcohol/$NH_3$ are continuously distilled from the reactor and replaced with urea and fresh or recycled alcohol.

In the second step the alkyl carbamate synthesized in the first step or obtained elsewhere is reacted with an alcohol (i.e., the alcohol may be either the same or different from the alcohol used in the carbamate synthesis step or a mixture of various alcohols) in the presence of the dialkyltin dialkoxide catalyst of the present invention to form dialkyl carbonate and $NH_3$. The alcohol and the formed dialkyl carbonate are distilled from the reactor and the alkyl carbamate/alcohol solution is fed to replace that which is removed by distillation. Under these conditions, virtually no by-products (i.e., alkylation products of the starting material) are formed and alkyl carbamate is quantitatively converted to dialkyl carbonate.

To avoid the formation of N-alkyl by-products during the carbonate synthesis process the following critical operating parameters must be adhered to: (1) addition of catalyst in an amount in the range between about 5 to 50 weight % based on the entire reaction solution (more preferably between about 10–25 weight %), (2) maintaining very low free alcohol concentration in the reaction solution of about 10 to 30 weight % based on total carbamate and alcohol content of the reactor solution, (3) maintaining a carbamate concentration in the range between about 70–90 weight % based on total carbamate and alcohol content of the reactor solution, and (4) distilling off dialkyl carbonate product such that it has a concentration of between about 1 to 3 weight % based on total carbamate and alcohol content of the reactor solution. The alkyl carbamate to alcohol molar ratio is preferably in the range between about 2:1 and 10:1, more prefer ably between about 3:1 and 5:1.

It is also desirable to maintain the temperature of the carbonate reactor in the range between about 140° C. to 220° C. The pressure of the reactor is autogenous, i.e., the sum of the vapor pressure of the alcohol, ammonia and alkyl carbamate at the reaction temperature.

The reactivation or regeneration of spent tin catalyst by treatment thereof with water, follow ed by alcohol and alkyl carbamate is also suitable for various other applications such as transesterification, esterification, ester interchange and transamination.

EXAMPLE 1

For comparative purposes, the $^{119}Sn$ nmr spectrum of a sample of $Bu_2Sn(OMe)_2$ obtained from Aldrich Chemical Company was recorded and demonstrated a singlet at −160 ppm.

EXAMPLE 2

A mixture containing 338 grams of methyl carbamate, 144 grams of methanol and 308 grams of dibutyltin oxide was placed in a one-liter autoclave. The autoclave was set at a back pressure of 1.121 MPa (148 psig) then heated to an average temperature of 165° C. The volatile components generated by the reaction along with methanol were collected in a knock-out vessel placed downstream of the autoclave. Fresh methanol was continuously added to replace that taken overhead. After seven hours a sample of the reactor mixture was analyzed by nmr and showed a resonance peak at −155 ppm, indicating the presence of $Bu_2Sn(OMe)_2$, i.e., a dibutyltin dimethoxide.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. A process for making a catalyst product which comprises reacting dialkyltin oxide with an alcohol and the corresponding alkyl carbamate at a temperature in the range between about 160 to 190° C. and at an autogenous pressure, wherein said catalyst product comprises dialkyltin dialkoxide in the range between about 50 to 100 mole % based on the tin species of said catalyst product.

2. The process according to claim 1 wherein said dialkyltin oxide is dibutyltin oxide.

3. The process according to claim 1 wherein said alkyl carbamate is methyl carbamate.

4. The process according to claim 1 wherein the reaction occurs for a period of between about 1 to 6 hours.

5. The process according to claim 1 wherein said dialkyltin dialkoxide is dibutyltin dimethoxide.

6. The process according to claim 1 wherein said catalyst product comprises dialkyltin dialkoxide in the range between about 70 to 100 mole % based on the tin species of said catalyst product.

7. The process according to claim 6 wherein said catalyst product comprises dialkyltin dialkoxide in the range between about 90 to 98 mole % based on the tin species of said catalyst product.

8. The process according to claim 1 wherein said alcohol is a primary alcohol selected from the group consisting of: $C_1$ to $C_{12}$ primary alcohols.

9. The process according to claim 1 wherein said alcohol is a secondary alcohol selected from the group consisting of $C_1$ to $C_{12}$ secondary alcohols.

10. The process according to claim 1 wherein said dialkyltin oxide is present in an amount of about 1 to 25 mole %, based on the total reaction mixture, said alcohol is present in an amount of about 10 to 90 mole %, based on the total reaction mixture, and said alkyl carbamate is present in an amount of about 20 to 90 mole %, based on the total reaction mixture.

11. The process according to claim 1 wherein the molar ratio of said alcohol to said alkyl carbamate is in the range between about 10:1 to 1:4.

12. A process for making a catalyst product which comprises reacting an alcohol and urea in the presence of dialkyltin oxide at a temperature in the range between about 155 to 190° C. and at an autogenous pressure, thereby forming an alkyl carbamate in-situ which reacts with said dialkyltin oxide to form said catalyst product which comprises dialkyltin dialkoxide in the range between about 50 to 100 mole % based on the tin species of said catalyst product.

13. The process according to claim 12 wherein said dialkyltin oxide is dibutyltin oxide.

14. The process according to claim 12 wherein said alkyl carbamate is methyl carbamate.

15. The process according to claim 12 wherein the reaction occurs for a period of between about 6 to 8 hours.

16. The process according to claim 12 wherein said dialkyltin dialkoxide is dibutyltin dimethoxide.

17. The process according to claim 12 wherein said catalyst product comprises dialkyltin dialkoxide in the range between about 70 to 100 mole % based on the tin species of said catalyst product.

18. The process according to claim 17 wherein said catalyst product comprises dialkyltin dialkoxide in the range between about 90 to 98 mole % based on the tin species of said catalyst product.

19. The process according to claim 12 wherein said alcohol is a primary alcohol selected from the group consisting of $C_1$ to $C_{12}$ primary alcohols.

20. The process according to claim 12 wherein said alcohol is a secondary alcohol selected from the group consisting of $C_1$ to $C_{12}$ secondary alcohols.

21. The process according to claim 12 wherein the molar ratio of said alcohol to said urea is in the range between about 10:1 to 1:1.

* * * * *